US010189008B2

(12) United States Patent
Wattebled et al.

(10) Patent No.: US 10,189,008 B2
(45) Date of Patent: Jan. 29, 2019

(54) ODOR AND COLOR STABLE WATER-ABSORBING COMPOSITION

(71) Applicant: Evonik Degussa GmbH, Essen (DE)

(72) Inventors: Laurent Wattebled, Dusseldorf (DE); Jessica Pillat, Krefeld (DE); Lisa Maus, Krefeld (DE); Scott Smith, Dusseldorf (DE); Jorg Harren, Baesweiler (DE)

(73) Assignee: Evonik Degussa GmbH, Essen (DE)

( * ) Notice: Subject to any disclaimer, the term of this patent is extended or adjusted under 35 U.S.C. 154(b) by 258 days.

(21) Appl. No.: 14/434,322

(22) PCT Filed: Oct. 24, 2013

(86) PCT No.: PCT/EP2013/072229
§ 371 (c)(1),
(2) Date: Apr. 8, 2015

(87) PCT Pub. No.: WO2014/064176
PCT Pub. Date: May 1, 2014

(65) Prior Publication Data

US 2015/0258527 A1 Sep. 17, 2015

(30) Foreign Application Priority Data

Oct. 24, 2012 (DE) ........................ 10 2012 219 378

(51) Int. Cl.

| | |
|---|---|
| ***B01J 20/26*** | (2006.01) |
| ***B01J 20/02*** | (2006.01) |
| ***B01J 20/22*** | (2006.01) |
| ***B01J 20/30*** | (2006.01) |
| ***A61L 15/42*** | (2006.01) |
| ***A61L 15/60*** | (2006.01) |
| ***C08F 220/06*** | (2006.01) |
| ***C08K 5/13*** | (2006.01) |
| ***C08K 5/14*** | (2006.01) |
| ***A61L 15/24*** | (2006.01) |
| *C08K 3/011* | (2018.01) |

(52) U.S. Cl.
CPC ............... *B01J 20/26* (2013.01); *A61L 15/24* (2013.01); *A61L 15/42* (2013.01); *A61L 15/60* (2013.01); *B01J 20/02* (2013.01); *B01J 20/22* (2013.01); *B01J 20/261* (2013.01); *B01J 20/265* (2013.01); *B01J 20/267* (2013.01); *B01J 20/3042* (2013.01); *C08F 220/06* (2013.01); *C08K 5/13* (2013.01); *C08K 5/14* (2013.01); *B01J 2220/68* (2013.01); *C08K 3/011* (2018.01)

(58) Field of Classification Search
None
See application file for complete search history.

(56) References Cited

U.S. PATENT DOCUMENTS

| | | | | |
|---|---|---|---|---|
| 4,363,322 | A | 12/1982 | Andersson | |
| 5,314,420 | A | 5/1994 | Smith et al. | |
| 5,399,591 | A | 3/1995 | Smith et al. | |
| 5,451,613 | A | 9/1995 | Smith et al. | |
| 5,462,972 | A | 10/1995 | Smith et al. | |
| 6,025,186 | A * | 2/2000 | Kirk ........................ | A61L 15/38 424/94.4 |
| 6,444,744 | B1 * | 9/2002 | Fujimaru ................ | A61L 15/24 524/556 |
| 6,605,673 | B1 | 8/2003 | Harren et al. | |
| 6,620,889 | B1 | 9/2003 | Harren et al. | |
| 6,623,848 | B2 | 9/2003 | Harren et al. | |
| 6,649,805 | B1 | 11/2003 | Carlucci et al. | |
| 6,831,142 | B2 | 12/2004 | Harren et al. | |
| 6,906,131 | B2 | 6/2005 | Ahmed et al. | |
| 7,026,373 | B2 | 4/2006 | Kang et al. | |
| 7,163,969 | B2 | 1/2007 | Ahmed et al. | |
| 7,169,843 | B2 | 1/2007 | Frank et al. | |

(Continued)

FOREIGN PATENT DOCUMENTS

| | | | |
|---|---|---|---|
| CA | 2460152 | A1 | 10/2009 |
| CN | ZL02819951 | | 8/2007 |

(Continued)

OTHER PUBLICATIONS

Buchholz et al., "Modern Superabsorbent Polymer Technology," Wiley, 1998, pp. 24 and 39-44.

(Continued)

*Primary Examiner* — Joseph D Anthony
(74) *Attorney, Agent, or Firm* — Bernard Lau; Jason S. Ngul; Linda S. Li

(57) ABSTRACT

The present invention relates to a water-absorbing composition comprising at least i) 89 to 99.89 wt % of at least one water-absorbing polymer;

ii) 0.1 to 10 wt % of at least one oxidizing agent;

iii) 0.01 to 1 wt % of at least one inhibitor to inhibit free-radical polymerizations;

wherein the weight quantities are each based on the overall weight of the water-absorbing composition.

The present invention also relates to a process for producing a water-absorbing composition, the water-absorbing composition obtainable by this process, a composite, a process for producing a composite, the composite obtainable by this process, chemical products such as foams, moldings, fibers, foils, films, cables, sealing materials, liquid-imbibing hygiene articles, carriers for plant and fungal growth regulators, packaging materials, soil additives or building products and also the use of a water-absorbing composition.

16 Claims, No Drawings

(56) References Cited

U.S. PATENT DOCUMENTS

| | | | |
|---|---|---|---|
| 7,173,086 | B2 | 2/2007 | Bremus et al. |
| 7,179,862 | B2 | 2/2007 | Harren et al. |
| 7,241,820 | B2 | 7/2007 | Smith et al. |
| 7,285,599 | B2 | 10/2007 | Harren et al. |
| 7,291,674 | B2 | 11/2007 | Kang et al. |
| 7,312,286 | B2 | 12/2007 | Smith et al. |
| 7,335,713 | B2 | 2/2008 | Smith et al. |
| 7,399,813 | B2 | 7/2008 | Smith et al. |
| 7,427,650 | B2 | 9/2008 | Frank et al. |
| 7,482,058 | B2 | 1/2009 | Ahmed et al. |
| 7,488,541 | B2 | 2/2009 | Ahmed et al. |
| 7,572,864 | B2 | 8/2009 | Harren et al. |
| 7,579,402 | B2 | 8/2009 | Ahmed et al. |
| 7,625,957 | B2 | 12/2009 | Harren et al. |
| 7,728,079 | B2 | 6/2010 | Harren et al. |
| 7,777,093 | B2 | 8/2010 | Bremus et al. |
| 7,795,345 | B2 | 9/2010 | Frank et al. |
| 7,812,082 | B2 | 10/2010 | Bergman et al. |
| 7,816,426 | B2 | 10/2010 | Walden et al. |
| 7,833,624 | B2 | 11/2010 | Brehm et al. |
| 7,842,386 | B2 | 11/2010 | Bremus et al. |
| 7,906,585 | B2 | 3/2011 | Bergman et al. |
| 7,910,688 | B2 | 3/2011 | Tian et al. |
| 8,048,942 | B2 | 11/2011 | Gartner et al. |
| 8,063,118 | B2 | 11/2011 | Walden et al. |
| 8,063,121 | B2 | 11/2011 | Gartner et al. |
| 8,198,385 | B2 | 6/2012 | Gartner et al. |
| 8,222,477 | B2 | 7/2012 | Azad et al. |
| 8,236,876 | B2 | 8/2012 | Walden et al. |
| 8,236,884 | B2 | 8/2012 | Smith et al. |
| 8,252,873 | B1 | 8/2012 | Gartner et al. |
| 8,288,002 | B2 | 10/2012 | Bremus et al. |
| 8,309,682 | B2 | 11/2012 | Tian et al. |
| 8,318,306 | B2 | 11/2012 | Tian et al. |
| 8,318,895 | B1 | 11/2012 | Tian et al. |
| 8,349,913 | B2 | 1/2013 | Harren et al. |
| 8,357,766 | B2 | 1/2013 | Gartner et al. |
| 8,361,926 | B2 | 1/2013 | Tian et al. |
| 8,445,596 | B2 | 5/2013 | Harren et al. |
| 8,466,228 | B2 | 6/2013 | Frank et al. |
| 8,486,855 | B2 | 7/2013 | Tian et al. |
| 8,487,049 | B2 | 7/2013 | Tian et al. |
| 8,518,541 | B2 | 8/2013 | Bremus et al. |
| 8,519,041 | B2 | 8/2013 | Smith et al. |
| 8,580,953 | B2 | 11/2013 | Frank et al. |
| 8,653,210 | B2 | 2/2014 | Gartner et al. |
| 8,658,146 | B2 | 2/2014 | Furno et al. |
| 8,686,216 | B2 | 4/2014 | Wattebled et al. |
| 8,703,645 | B2 | 4/2014 | Tian et al. |
| 8,734,948 | B2 | 5/2014 | Tian et al. |
| 8,802,786 | B2 | 8/2014 | Shi et al. |
| 8,822,582 | B2 | 9/2014 | Smith et al. |
| 8,859,701 | B2 | 10/2014 | Loick et al. |
| 8,859,758 | B2 | 10/2014 | Frank et al. |
| 8,883,881 | B2 | 11/2014 | Bremus et al. |
| 8,906,824 | B2 | 12/2014 | Loeker et al. |
| 8,906,837 | B2 | 12/2014 | Allef et al. |
| 8,962,910 | B2 | 2/2015 | Azad et al. |
| 2004/0019342 | A1* | 1/2004 | Nagasuna ......... A61F 13/15203 604/385.01 |
| 2004/0024104 | A1 | 2/2004 | Ota et al. |
| 2004/0236049 | A1* | 11/2004 | Fuchs ..................... A61L 15/24 526/317.1 |
| 2005/0085604 | A1 | 4/2005 | Handa et al. |
| 2007/0065503 | A1 | 3/2007 | Harren et al. |
| 2009/0148686 | A1* | 6/2009 | Urankar .................. A61L 15/46 428/304.4 |
| 2010/0036004 | A1 | 2/2010 | Harren et al. |
| 2010/0099799 | A1* | 4/2010 | Fricker ..................... C08F 2/16 523/348 |
| 2010/0105808 | A1* | 4/2010 | Fricker ..................... C08F 2/14 523/343 |
| 2010/0279860 | A1 | 4/2010 | Bremus et al. |
| 2010/0197877 | A1* | 8/2010 | Funk ..................... C08F 220/06 526/317.1 |
| 2011/0053767 | A1 | 3/2011 | Braig et al. |
| 2012/0001122 | A1 | 1/2012 | Wattebled et al. |
| 2012/0302445 | A1 | 11/2012 | Rudolph et al. |
| 2013/0136713 | A1 | 5/2013 | Terada et al. |
| 2014/0045683 | A1* | 2/2014 | Loick ...................... A61L 15/22 502/402 |
| 2014/0054497 | A1 | 2/2014 | Wattebled et al. |
| 2014/0121322 | A1 | 5/2014 | Gartner et al. |
| 2014/0257223 | A1 | 9/2014 | Henn et al. |
| 2014/0306155 | A1 | 10/2014 | Tian et al. |
| 2014/0306156 | A1 | 10/2014 | Tian et al. |
| 2014/0309607 | A1 | 10/2014 | Tian et al. |
| 2014/0312273 | A1 | 10/2014 | Wattebled et al. |
| 2014/0316040 | A1 | 10/2014 | Shi et al. |
| 2015/0258527 | A1* | 9/2015 | Wattebled .............. A61L 15/24 252/194 |

FOREIGN PATENT DOCUMENTS

| | | | |
|---|---|---|---|
| CN | 101868258 | A | 10/2010 |
| EP | 0942014 | A2 | 9/1999 |
| EP | 1438354 | B1 | 11/2010 |
| GB | 627512 | A | 8/1949 |
| GB | 2377890 | A | 1/2003 |
| JP | H04331205 | A | 11/1992 |
| JP | 2005225921 | A | 8/2005 |
| TW | I306411 | B | 2/2009 |
| TW | 201215416 | A | 4/2012 |
| TW | 201503918 | A | 2/2015 |
| WO | 9505856 | A1 | 3/1995 |
| WO | 9908726 | A1 | 2/1999 |
| WO | 2003051940 | A1 | 6/2003 |
| WO | 2009066255 | A2 | 5/2009 |
| WO | 2010096595 | A2 | 8/2010 |
| WO | 2014168858 | A1 | 10/2014 |

OTHER PUBLICATIONS

German language Search Report dated Apr. 2, 2013 in DE 10 2012 219 378.2 (5 pages).

German language Written Opinion dated Apr. 24, 2015 in PCT/EP2013/072229 (9 pages).

International Search Report dated Jan. 3, 2014 in PCT/EP2013/072229 (3 pages).

International Search Report dated Mar. 29, 2011 in PCT/EP2011/050713 (3 pages).

Written Opinion dated Jan. 3, 2014 in PCT/EP/2013/072229 (11 pages).

* cited by examiner

ODOR AND COLOR STABLE WATER-ABSORBING COMPOSITION

This application is a national stage application under 35 U.S.C. § 371 of International Application No. PCT/EP2013/072229 filed 24 Oct. 2013, which claims priority to German Application No. DE 10 2012 219 378.2 filed 24 Oct. 2012, the disclosures of which are expressly incorporated herein by reference.

FIELD

The present invention concerns a water-absorbing composition, a process for producing a water-absorbing composition, the water-absorbing composition obtainable by this process, a composite, a process for producing a composite, the composite obtainable by this process, chemical products such as foams, moldings, fibers, foils, films, cables, sealing materials, liquid-imbibing hygiene articles, carriers for plant and fungal growth regulators, packaging materials, soil additives or building products and also the use of a water-absorbing composition.

BACKGROUND

Superabsorbents are water-soluble, crosslinked polymers capable of imbibing and retaining, under pressure, large amounts of water, aqueous fluids, especially bodily fluids, preferably urine or blood, by swelling and forming hydrogels. Superabsorbents preferably absorb not less than 100 times of their own weight of water. Further details regarding superabsorbents are disclosed in "Modern Superabsorbent Polymer Technology", F. L. Buchholz, A. T. Graham, Wiley-VCH, 1998. Owing to these characteristic properties, these water-absorbing polymers are mainly incorporated in sanitary articles such as, for example, baby diapers, incontinence products or sanitary napkins.

Superabsorbents currently commercially available comprise essentially crosslinked polyacrylic acids or crosslinked starch-acrylic acid graft polymers wherein the carboxyl groups are partly neutralized with aqueous sodium or potassium hydroxide solution. These are obtainable by monomeric acrylic acid and/or salts thereof being free-radically polymerized in the presence of suitable crosslinking agents. Different methods of polymerization can find utility here, examples being the method of solution polymerization, the method of emulsion polymerization or the method of suspension polymerization. These different methods ultimately yield water-absorbing polymers in particulate form having a particle diameter ranging from 150 to 850 μm, which are then incorporated in sanitary articles.

However, superabsorbents of this type have a tendency to degrade in color after long periods of storage. The tendency of a superabsorbent to undergo a color transition from a clean, crisp, white color to a honey-brown color accelerates as storage time, temperature and humidity increase. In temperate climes, such as the United States of America and Europe, the rate at which a superabsorbent undergoes color degradation is sufficiently slow such that the superabsorbent, or the article containing the superabsorbent, typically is consumed before a color change is observable to the naked eye. However, in tropical and subtropical climates, such as South America and South East Asia, superabsorbent color degradation is sufficiently rapid such that a color change often occurs before the superabsorbent, or article containing the superabsorbent, is consumed.

The color degradation of the superabsorbent is blamed not only on the initiators used in the free-radical polymerization and remaining in the polymer, examples being ascorbic acid and sodium peroxodisulphate, and inhibitors generally included in the acrylic acid used for the purpose of inhibiting a spontaneous polymerization, an example being the monomethyl ether of hydroquinone (HQME), but also on certain added-substance materials admixed to superabsorbents after their production. Color stability has been found in this context to be particularly affected by oxidizing agents such as, for instance, sodium percarbonate which, as taught by WO-A-2009/066255, are admixed in particulate form to superabsorbents in order that the odor-forming properties of the superabsorbents may be ameliorated. When a superabsorbent containing hygiene article absorbs fluids, for example urine, unpleasant odors are generally quick to form due to the components of the urine, especially ammonia and other alkaline nitrogenous compounds. Bacterial growth can also lead to products which cause odor and/or lead to skin irritation. To address this problem, WO-A-2009/066255 proposes that oxidizing agents such as, for example, sodium percarbonate be incorporated in the hygiene article together with bleach activators. Preferably, the oxidizing agents are incorporated in the absorbent core of a hygiene article together with the superabsorbents. However, it has transpired here that the color stability of the superabsorbents is obviously affected by the presence of the oxidizing agents. Improved odor stability thus comes at the cost of reduced color stability.

The problem addressed by the present invention was accordingly that of overcoming the disadvantages apparent from the prior art.

The problem addressed by the present invention was more particularly that of specifying a water-absorbing composition characterized not only by an advantageous odor stability but also by an advantageous color stability.

The problem addressed by the present invention was also that of specifying a process for producing an advantageous water-absorbing composition of this type.

SUMMARY

A contribution to solving the problem as defined at the outset is made by a water-absorbing composition comprising at least i) 89 to 99.89 wt %, more preferably 91.2 to 98.9 wt % and most preferably 94.5 to 97.8 wt % of at least one water-absorbing polymer;
ii) 0.1 to 10 wt %, more preferably 1 to 8 wt % and most preferably 2 to 5 wt % of at least one oxidizing agent;
iii) 0.01 to 1 wt %, more preferably 0.1 to 0.75 wt % and most preferably 0.2 to 0.5 wt % of at least one inhibitor to inhibit free-radical polymerizations, wherein the weight quantities are each based on the overall weight of the water-absorbing composition.

In a particular embodiment of the water-absorbing composition according to the present invention, the weight ratio of component iii) to component ii) is in a range from 1:20 to 1:1, more preferably in a range from 1:15 to 1:2 and most preferably in a range from 1:10 to 1:4.

It was a complete surprise to find that the adverse effect of oxidizing agents such as, for example, sodium percarbonate on the color stability of superabsorbents can be reduced by additionally contacting the superabsorbents with polymerization inhibitors such as, for example, hydroquinone monomethyl ether (HQME). This is surprising because polymerization inhibitors such as HQME, with which the acrylic acid used for producing superabsorbents is typically additized to inhibit in particular a spontaneous polymerization of the acrylic acid, are themselves ascribed an adverse effect on color stability in the prior art.

DETAILED DESCRIPTION

The water-absorbing composition of the present invention comprises at least one water-absorbing polymer as component i).

The preference of the present invention is for water-absorbing polymers i) that are fibers, foams or particles, preferably fibers and particles and more preferably particles.

Polymeric fibers preferred according to the present invention are dimensioned such that they can be incorporated in or as yarns for textiles and also directly in textiles. It is preferable according to the present invention for the polymeric fibers to have a length in the range from 1 to 500 mm, preferably 2 to 500 mm and more preferably 5 to 100 mm and a diameter in the range from 1 to 200 denier, preferably from 3 to 100 denier and more preferably 5 to 60 denier.

Particulate water-absorbing polymers i) preferred according to the present invention are dimensioned such that they have a WSP 220.2 mean particle size in the range from 10 to 3000 μm, preferably 20 to 2000 μm and more preferably 150 to 850 μm. It is particularly preferable here for at least 90 wt % of the particles of the water-absorbing polymer i) to have a particle size in a range from 150 to 850 μm. In a particular embodiment of the water-absorbing polymers i), the fraction of polymer particles having a particle size in a range from 300 to 600 μm is at least 50 wt %, more preferably at least 65 wt % and most preferably at least 80 wt %, based on the overall weight of water-absorbing polymers i).

The water-absorbing polymer i) is preferably based on crosslinked and at least partially neutralized polyacrylic acid. It is particularly preferable in this context for the water-absorbing polymer i) to be based on polymerized acrylic acid to an extent of at least 50 wt %, preferably at least 70 wt % and more preferably at least 90 wt %, all based on the weight of the polymers. It is further preferable according to the present invention for the water-absorbing polymers i) to be based to an extent of at least 50 wt %, preferably at least 70 wt %, both based on the weight of the polymer materials, on polymerized acrylic acid which is preferably at least 20 mol %, more preferably at least 50 mol % and even more preferably from 60 to 85 mol % neutralized.

The water-absorbing polymers i) are preferably obtainable by a process comprising the steps of:

a) free-radically polymerizing an aqueous monomer solution comprising a polymerizable, monoethylenically unsaturated acid-functional monomer (α1) or a salt thereof, optionally a monoethylenically unsaturated monomer (α2) polymerizable with monomer (α1) and also at least one crosslinker (α3) to obtain a hydrogel;
b) optionally comminuting the hydrogel;
c) drying the optionally comminuted hydrogel to obtain particulate water-absorbing polymers;
d) optionally grinding and screening the resulting particulate water-absorbing polymers;
e) surface postcrosslinking the particulate water-absorbing polymers thus obtained with a crosslinker having at least two functional groups capable of reacting with the acid groups on the surface of the polymer materials.

Process step a) comprises the initial free-radical polymerization of an aqueous monomer solution comprising a polymerizable, monoethylenically unsaturated acid-functional monomer (α1) or a salt thereof, optionally a monoethylenically unsaturated monomer (α2) polymerizable with monomer (α1) and also at least one crosslinker (α3) to obtain a polymer gel. The monoethylenically unsaturated acid-functional monomers (α1) may be in a partially or completely, preferably partially, neutralized state. Preferably, the monoethylenically unsaturated acid-functional monomers (α1) are at least 25 mol %, more preferably at least 50 mol % and most preferably 50-80 mol % neutralized. The disclosure of DE 195 29 348 A1 in this context is hereby incorporated herein by reference. The neutralization may also be effected partly or wholly after the polymerization. Neutralization may further be effected using alkali metal hydroxides, alkaline earth metal hydroxides, ammonia and also carbonates and bicarbonates. Any further base capable of combining with the acid to form a water-soluble salt is also conceivable. Mixed neutralization with different bases is also conceivable. Preference is given to neutralization with a combination of carbonates and/or bicarbonates (which also act as blowing or pneumatogenic agents) and alkali metal hydroxides, more preferably with a combination of sodium carbonate and sodium hydroxide.

Preferred monoethylenically unsaturated acid-functional monomers (α1) are preferably those compounds which are recited in WO 2004/037903 A2, which is hereby incorporated by references and is therefore considered to be part of the disclosure, as ethylenically unsaturated acid-functional monomers (α1). Acrylic acid and methacrylic acid are particularly preferred monoethylenically unsaturated acid-functional monomers (α1), while acrylic acid is most preferable.

Acrylamides, methacrylamides or vinylamides can be used as monoethylenically unsaturated monomers (α2) copolymerizable with the monomers (α1). Further preferred co-monomers are especially those which in the—bearing monomers (α1) are preferably those compounds which are recited in WO 2004/037903 A2 as co-monomers (α2).

Crosslinkers (α3) preferably likewise utilize those compounds which WO 2004/037903 A2 as crosslinkers (α3). Of these crosslinkers, water-soluble crosslinkers are particularly preferred. N,N'-Methylenebisacrylamide, polyethylene glycol di(meth)acrylates, triallylmethylammonium chloride, tetraallylammonium chloride and also allyl nonaethylene glycol acrylate (prepared using 9 mol of ethylene oxide per mole of acrylic acid).

In addition to the monomers (α1) and optionally (α2) and also the at least one crosslinker (α3), the monomer solution may also comprise water-soluble polymers (α4). Preferred water-soluble polymers comprising partially or fully hydrolyzed polyvinyl alcohol, polyvinylpyrrolidone, starch or starch derivatives, polyglycols or polyacrylic acid. The molecular weight of these polymers is uncritical provided they are water-soluble. Starch or starch derivatives or polyvinyl alcohol are preferred water-soluble polymers. The water-soluble polymers, preferably synthetic water-soluble polymers such as polyvinyl alcohol, can serve not just as grafting base for the monomers to be polymerized. It is also conceivable for these water-soluble polymers to be admixed to the hydrogel only after the polymerization, or to the already dried, water-absorbing polymer.

The monomer solution may further also comprise auxiliaries (α5), these auxiliaries including especially the initiators or complexing agents which may be required for the polymerization, for example EDTA.

Useful solvents for the monomer solution include water, organic solvents or mixtures of water and organic solvents, the choice of solvent depending especially also on the manner of the polymerization.

The relative amount of monomers ($\alpha1$) and ($\alpha2$) and also of crosslinkers ($\alpha3$) and water-soluble polymers ($\alpha4$) and auxiliaries ($\alpha5$) in the monomer solution is preferably chosen such that the particulate water-absorbing polymer obtained after drying in process step iii) is based

- to an extent of 20 to 99.999 wt %, preferably to an extent of 55 to 98.99 wt % and more preferably to an extent of 70 to 98.79 wt % on the monomers ($\alpha1$),
- to an extent of 0 to 80 wt %, preferably to an extent of 0 to 44.99 wt % and more preferably to an extent of 0.1 to 44.89 wt % on the monomers ($\alpha2$),
- to an extent of 0 to 5 wt %, preferably to an extent of 0.001 to 3 wt % and more preferably to an extent of 0.01 to 2.5 wt % on the crosslinkers ($\alpha3$),
- to an extent of 0 to 30 wt %, preferably to an extent of 0 to 5 wt % and more preferably to an extent of 0.1 to 5 wt % on the water-soluble polymers ($\alpha4$),
- to an extent of 0 to 20 wt %, preferably to an extent of 0 to 10 wt % and more preferably to an extent of 0.1 to 8 wt % on the auxiliaries ($\alpha5$), and
- to an extent of 0.5 to 25 wt %, preferably to an extent of 1 to 10 wt % and more preferably to an extent of 3 to 7 wt % on water ($\alpha6$), where the sum total of the weights ($\alpha1$) to ($\alpha6$) is 100 wt %. Optimum values for the concentration especially of the monomers, of the crosslinkers and water-soluble polymers in the monomer solution can be determined by simple preliminary tests or else extracted from the prior art, especially the printed publications U.S. Pat. No. 4,286,082, DE-A-27 06 135, U.S. Pat. No. 4,076,663, DE-A-35 03 458, DE 40 20 780 Cl, DE-A-42 44 548, DE-A-43 33 056 and DE-A-44 18 818. The monomer solution can in principle be free-radically polymerized using any polymerization method known to a person skilled in the art. Suitable in this context are for example the method of solution polymerization, which is preferably carried out in kneading reactors such as extruders or continuously on a polymerization belt, the method of spray polymerization, the method of inverse emulsion polymerization and the method of inverse suspension polymerization.

Solution polymerization is preferably carried out in water as the solvent. Solution polymerization can be carried out as a continuous operation or as a batch operation. The prior art yields a broad spectrum of possible variations with regard to reaction conditions such as temperature, type and amount of initiators and also the reaction solution. Typical methods are described in the following patent documents: U.S. Pat. No. 4,286,082, DE-A-27 06 135 A1, U.S. Pat. No. 4,076,663, DE-A-35 03 458, DE 40 20 780 Cl, DE-A-42 44 548, DE-A-43 33 056, DE-A-44 18 818. The disclosures are hereby incorporated by reference and are therefore deemed part of the disclosure.

The polymerization is triggered by an initiator, as is generally customary. The initiators used to initiate the polymerization may be all initiators which form free radicals under the polymerization conditions and are typically used in the production of superabsorbents. Initiation of the polymerization by the action of electron beams on the polymerizable aqueous mixture is also possible. The polymerization can, however, also be triggered in the absence of initiators of the type mentioned above by the action of high-energy radiation in the presence of photoinitiators. Polymerization initiators may be present dissolved or dispersed in the monomer solution. Useful initiators include all compounds which decompose to free radicals and are known to the person skilled in the art. These include especially those initiators which are already mentioned in WO-A-2004/037903 as possible initiators. Particular preference is given to producing the water-absorbing polymer structures using a redox system consisting of hydrogen peroxide, sodium peroxodisulphate and ascorbic acid.

Inverse suspension and emulsion polymerization can also be employed to produce the water-absorbing polymers i). In these processes, an aqueous, partially neutralized solution of the monomers ($\alpha1$) and also optionally comprising the further monomers ($\alpha2$), the water-soluble polymers ($\alpha4$) and auxiliaries ($\alpha5$), is dispersed with the aid of protective colloids and/or emulsifiers in a hydrophobic organic solvent, and the polymerization is initiated by means of free-radical initiators. The crosslinkers ($\alpha3$) are either dissolved in the monomer solution and are added together with it, or else are added separately and optionally during the polymerization. Optionally, a water-soluble polymer ($\alpha4$) is added as a grafting base via the monomer solution, or by direct initial charging into the oil base. Subsequently, the water is azeotropically removed from the mixture and the polymer is filtered off.

In addition, both in the case of solution polymerization and in the case of inverse suspension and emulsion polymerization, the crosslinking can be effected by copolymerization of the polyfunctional crosslinker ($\alpha3$) dissolved in the monomer solution and/or by reaction of suitable crosslinkers with functional groups of the polymer during the polymerization steps. The processes are described, for example, in publications U.S. Pat. No. 4,340,706, DE-A-37 13 601, DE-A-28 40 010 and WO-A-96/05234, the corresponding disclosure of which is hereby incorporated by reference.

In process step b), the hydrogel obtained in process step a) is optionally comminuted, this comminution being done especially when the polymerization is performed by means of a solution polymerization. Comminution can be effected by means of comminution apparatus known to those skilled in the art, for instance a meat grinder.

In process step c), the hydrogel which has optionally been comminuted beforehand is dried. The hydrogel is preferably dried in suitable driers or ovens. Examples include rotary tube ovens, fluidized bed driers, pan driers, paddle driers or infrared driers. It is additionally preferred in accordance with the invention that the hydrogel is dried in process step c) down to a water content of 0.5 to 25% by weight, preferably of 1 to 10% by weight, the drying temperatures typically being within a range from 100 to 200° C.

In process step d), the particulate water-absorbing polymers which are obtained in process step c), especially when they have been obtained by solution polymerization, can be ground and screened off to the desired particle size specified at the outset. The dried water-absorbing polymers are preferably ground in suitable mechanical comminuting devices, for example a ball mill, while screening off can be effected for example by using screens of suitable mesh size.

In process step e), the optionally ground and screened-off particulate water-absorbing polymers are surface postcrosslinked with a crosslinker having two or more functional groups capable of reacting with the acid groups on the surface of the polymer materials, and the surface of the polymers is brought into contact with aluminum salts, preferably with aluminum lactate and/or aluminum sulphate, before, during or after the postcrosslinking.

For surface postcrosslinking, the dried and optionally ground and screened-off particulate water-absorbing polymers, from process steps c) or d), or else the undried, but preferably already comminuted hydrogel, from process step b), are brought into contact with a preferably organic, chemical surface postcrosslinker. Especially when the postcrosslinker is not liquid under the postcrosslinking conditions, it is preferably contacted with the particulate water-absorbing polymer or the optionally comminuted hydrogel in the form of a fluid comprising the postcrosslinker and a solvent. The solvents used are preferably water, water-miscible organic solvents, for instance methanol, ethanol, 1-propanol, 2-propanol or 1-butanol or mixtures of at least two of these solvents, water being the most preferred solvent. It is additionally preferred that the postcrosslinker is present in the fluid in an amount within a range from 5 to 75 wt %, more preferably 10 to 50 wt % and most preferably 15 to 40 wt %, based on the total weight of the fluid.

The contacting of the particulate water-absorbing polymer or of the optionally comminuted hydrogel, with the fluid containing the postcrosslinker is preferably effected by thorough mixing of the fluid with the polymer material and hydrogel, respectively.

Suitable mixing units for applying the fluid are, for example, the Patterson-Kelley mixer, DRAIS turbulent mixers, Lodige mixers, Ruberg mixers, screw mixers, pan mixers and fluidized bed mixers, and also continuous vertical mixers in which the polymer material is mixed at high frequency by means of rotating blades (Schugi mixer).

The particulate water-absorbing polymer or the optionally comminuted hydrogel is preferably contacted at postcrosslinking with not more than 20 wt %, more preferably with not more than 15 wt %, even more preferably with not more than 10 wt % and yet even more preferably with not more than 5 wt % of solvent, preferably water.

In the case of polymer materials in the form of preferably spherical particles, it is further preferable according to the present invention for the contacting to be effected such that only the outer region but not the inner region of the particulate polymers is brought into contact with the fluid and hence the postcrosslinker.

Postcrosslinkers are preferably understood to mean compounds which have at least two functional groups which can react with the acid groups on the surface of the polymer in a condensation reaction (=condensation crosslinkers), in an addition reaction or in a ring-opening reaction. Preferred postcrosslinkers are those specified in WO-A-2004/037903 as crosslinkers of crosslinker classes II.

Among these compounds, particularly preferred postcrosslinkers are condensation crosslinkers, for example diethylene glycol, triethylene glycol, polyethylene glycol, glycerol, polyglycerol, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxolan-2-one.

Once the particulate water-absorbing polymers, or the optionally comminuted hydrogels, have been brought into contact with the postcrosslinker or with the fluid including the postcrosslinker, they are heated to a temperature in the range from 50 to 300° C., preferably 75 to 275° C. and more preferably 150 to 250° C., such that, preferably as a result of which, the outer region of the particles of the polymer is more highly crosslinked compared to the inner region (=postcrosslinking), and, when a hydrogel are used, they are simultaneously also dried. The duration of the heat treatment is limited by the risk that the desired profile of properties of the polymer is destroyed owing to the action of heat.

Before, during or after the postcrosslinking step, the surface of the polymers, or of the optionally comminuted hydrogel, is brought into contact with aluminum salts, preferably with aluminum lactate. It is particularly preferable for the treatment with the aluminum salts to be carried out at the same time as the surface postcrosslinking step by bringing a preferably aqueous solution containing the postcrosslinker and also the aluminum salt(s), preferably aluminum lactate, into contact with the water-absorbing polymer, or with the hydrogel, and then heating.

It is preferable here for the aluminum salts to be brought into contact with the polymer/hydrogel in an amount ranging from 0.01 to 30 wt %, more preferably in an amount ranging from 0.1 to 20 wt % and even more preferably in an amount ranging from 0.3 to 5 wt % (if present as hydrate, reckoned on an anhydrous basis), all based on the weight of the water-absorbing polymer or, respectively, of the optionally comminuted hydrogel.

Preferred aluminum salts are particularly $AlCl_3 \times 6H_2O$, $NaAl(SO_4)_2 \times 12\ H_2O$, $KAl(SO_4)_2 \times 12\ H_2O$ or $Al_2(SO_4)_3 \times$ 14-18 $H_2O$, aluminum lactate or else water-insoluble aluminum compounds, for instance aluminum oxides, for example $Al_2O_3$, or aluminates. Particular preference is given to using aluminum lactate, aluminum sulphate or mixtures of aluminum lactate and aluminum sulphate.

The composition according to the present invention further comprises at least one oxidizing agent as component ii), hydrogen peroxide sources in particular being preferred as oxidizing agents.

In principle, useful hydrogen peroxide sources include any oxidizing agents which have an advantageous effect on the odor stability of the water-absorbing composition and the hydrogen peroxide sources mentioned as suitable hydrogen peroxide sources in WO-A-2009/066255. Particular preference is accordingly given to perborates such as, for instance, sodium perborate (including the hydrates such as for instance the mono- or tetrahydrate), sodium carbonate peroxyhydrate, sodium pyrophosphate peroxyhydrate, urea peroxyhydrate, sodium peroxide, percarbonates such as sodium percarbonate, stable complexes of polyvinylpyrrolidone with hydrogen peroxide, as described in US-A-2006/0292091, stable crystalline complexes of carbohydrates and hydrogen peroxide, as described in U.S. Pat. No. 6,887,496, or mixtures of two or more of these hydrogen peroxide sources. Use of sodium percarbonate as oxidizing agent is particularly preferred according to the present invention.

It is further preferable according to the present invention for the oxidizing agent to be likewise present in particulate form in the composition according to the present invention, in that it has been found to be advantageous for at least 80 wt %, even more preferably at least 90 wt % and most preferably at least 100 wt % of the particles of the oxidizing agent, preferably of the sodium percarbonate particles, to have a particle size in the range from 400 to 800 μm, while the particle size weight average as determined by sieve analysis is preferably in a range from 500 to 800 μm.

The water-absorbing composition according to the present invention further comprises, as component iii), at least one inhibitor to inhibit free-radical polymerizations, especially an inhibitor to inhibit the free-radical polymerization of acrylic acid, this inhibitor preferably being hydroquinone or a hydroquinone derivative. The mono- or diether derivatives are preferred derivatives of hydroquinone in this context.

Inhibitors particularly preferred according to the present invention are selected from the group consisting of hydroquinone, hydroquinone monomethyl ether (HQME), 1,4-dimethoxybenzene, 4,4'-oxydiphenol and a mixture of two or more thereof, HQME being the most preferred inhibitor.

In the water-absorbing composition according to the present invention, the inhibitor iii) is preferably not uniformly distributed within the preferably particulate water-absorbing polymer (such a uniform distribution is obtained when the only inhibitor in the composition was already present before the polymerization as additized in the acrylic acid), but has a higher concentration in the surface region than in the core of the preferably particulate water-absorbing polymer (such a noneven distribution is obtained when the composition also comprises an inhibitor which is brought into contact with the particulate water-absorbing polymer preferably by simple mixing only after completion of the polymerization reaction, especially only after process step c) and especially only after process step e) of the above-described process for producing the water-absorbing polymers).

In one particular embodiment of the water-absorbing composition according to the present invention, said composition in addition to the water-absorbing polymers i), the oxidizing agent ii) and the inhibitor iii) may comprise as further component iv) at least one bleach activator, in which case useful bleach activators include particularly those bleach activators recited in WO-A-2009/066255 as suitable bleach activators. Preferred bleach activators in this connection are selected from the group consisting of tetraacetylethylenediamine (TAED), benzoylcaprolactam (BzCL), 4-nitrobenzoylcaprolactam, S-chlorobenzoylcaprolactam, benzoyloxybenzenesulphonate (BOBS), nonanoyloxybenzenesulphonate (NOBS), phenylbenzoate (PhBz), decanoyloxybenzenesulphonate ($C_{10}$ OBS), benzoylvalerolactam (BZVL), octanoyloxybenzenesulphonate ($C_8$ OBS) and mixtures of two or more thereof, of which the use of tetraacetylethylenediamine (TAED), nonanoylbenzenesulphonate (NOBS) or a mixture of two or more thereof is particularly preferable. The bleach activator, as likewise described in WO-A-2009/066255, may in accordance with the teaching of WO-A-2005/080542, be bonded to a particulate carrier via suitable binders. The amount of bleach activators, if present in the water-absorbing composition according to the present invention, is preferably determined such that the molar ratio of hydrogen peroxide (which is provided by the hydrogen peroxide source) to the bleach activator is in a range from 100:1 to 1:1 and more preferably in a range from 80:1 to 5:1.

The water-absorbing composition in accordance with the present invention is preferably characterized by a $\Delta L$ value, as determined by a test method described herein, of at most 10, more preferably at most 7.5 and most preferably of at most 5 after the water-absorbing composition has been stored at 70° C. and a relative humidity of 75% for 10 days. It is further preferable according to the present invention for the water-absorbing compositions according to the present invention to have a $\Delta L$ value which is at least 10, preferably at least 20 and most preferably at least 30 smaller than the $\Delta L$ value of the corresponding composition without component iii).

A contribution to solving the problems defined at the outset is also made by a process for producing a water-absorbing composition comprising at least the steps of:

(I) providing at least one water-absorbing polymer;

(II) contacting the at least one water-absorbing polymer with at least one oxidizing agent;

(III) contacting the at least one water-absorbing polymer with at least one inhibitor to inhibit free-radical polymerizations;

wherein step III) can be carried out before, during or after step II).

Process step (I) comprises initially providing at least one water-absorbing polymer, wherein those water-absorbing polymers are preferred as water-absorbing polymer which were already described at the outset as preferred water-absorbing polymers in connection with the water-absorbing composition according to the present invention. The water-absorbing polymers are preferably provided using the initially described process comprising steps a) to e). It is particularly preferable in this connection for at least process step (III), or preferably process steps (II) and (III), to be carried out only after completion of the postcrosslinking reaction as per process step e) of the initially described process for producing the water-absorbing polymers.

In process steps II) and III), the water-absorbing polymer, preferably the particles of the water-absorbing polymer, is then brought into contact with the oxidizing agent and with the inhibitor, respectively, wherein those compounds are again preferred for use as oxidizing agent and as inhibitor which were already mentioned at the outset as preferred oxidizing agent and as preferred inhibitor, respectively, in connection with the water-absorbing composition according to the present invention.

Not only the oxidizing agent but also the inhibitor can be brought into contact with the water-absorbing polymer as a solid or in the form of a solution or dispersion. The oxidizing agent and the inhibitor can further be brought into contact with the water-absorbing polymer in a conjoined solid mixture or else in a conjoined solution or dispersion or separately from each other in succession or concurrently, in which case mixing apparatus which appears suitable for this purpose to a person skilled in the art can be used for the purpose of bringing into contact.

The relative amounts in which the water-absorbing polymer, the oxidizing agent and the inhibitor are used are preferably determined so as to obtain a water-absorbing composition comprising i) 89 to 99.89 wt %, more preferably 91.2 to 98.9 wt % and most preferably 94.5 to 97.8 wt % of at least one water-absorbing polymer;

ii) 0.1 to 10 wt %, more preferably 1 to 8 wt % and most preferably 2 to 5 wt % of at least one oxidizing agent;

iii) 0.01 to 1 wt %, more preferably 0.1 to 0.75 wt % and most preferably 0.2 to 0.5 wt % of at least one inhibitor to inhibit free-radical polymerizations, wherein the weight quantities are each based on the overall weight of the water-absorbing composition.

In one particular embodiment of the process according to the present invention, said process comprises as further step:

IV) contacting the at least one water-absorbing polymer with at least one bleach activator, wherein those compounds are again preferable for use as bleach activator which were already mentioned at the outset as preferred bleach activators in connection with the water-absorbing composition according to the present invention. The remarks made in connection with the water-absorbing composition of the present invention are also referenced with regard to the manner of adding these bleach activators and also the relative amount in which these are used relative to the hydrogen peroxide.

A contribution to solving the problems mentioned at the outset is also made by an aqueous composition which is obtainable by the process according to the present invention.

Preferably, the composition obtainable by the process according to the present invention is characterized by a ΔL value, as determined by a test method described herein, of at most 10, more preferably of at most 7.5 and most preferably of at most 5 after the water-absorbing composition has been stored at 70° C. and relative humidity of 75% for 10 days. It is further preferable according to the present invention for the water-absorbing compositions obtainable by the process according to the present invention to have a ΔL value which is at least 10, preferably at least 20 and most preferably at least 30 smaller than the ΔL value of a composition obtained by the same process but without process step III).

A further contribution to solving the problems described at the beginning is also made by a composite comprising the water-absorbing composition according to the present invention, or the water-absorbing composition obtainable by the process according to the present invention, and a substrate. It is preferable for the water-absorbing composition, or the water-absorbing composition obtainable by the process according to the present invention, and the substrate to be firmly connected to each other. Preferred substrates are polymeric foils, for example foils composed of polyethylene, polypropylene or polyamide, metals, fibrous nonwoven webs, fluff, tissues, wovens, natural or synthetic fibers, or other foams. It is further preferable according to the present invention for the composite to encompass at least one region which comprises the water-absorbing composition according to the present invention, or the water-absorbing composition obtainable by the process according to the present invention, in an amount ranging from about 15 to 100 wt %, preferably about 30 to 100 wt %, more preferably about 50 to 99.99 wt %, more preferably about 60 to 99.99 wt % and even more preferably about 70 to 99 wt %, all based on the overall weight of the particular region of the composite, this region preferably having a size of at least 0.01 $cm^3$, preferably at least 0.1 $cm^3$ and most preferably at least 0.5 $cm^3$.

A particularly preferred embodiment of the composite according to the present invention comprises a sheetlike composite that is described in WO 02/056812 A1 as an "absorbent material". The disclosure content of WO 02/056812 A1, especially as regards the precise construction of the composite, the basis weight of the constituents of the composite and also the thickness of the composite is hereby incorporated herein by reference and forms part of the disclosure of the present invention.

A further contribution to solving the problems referred to at the outset is made by a process for producing a composite, said process comprising the water-absorbing to composition of the present invention, or the water-absorbing composition obtainable by the process according to the present invention, and a substrate and optionally an added-substance material being brought into contact with each other. The substrates used are preferably those substrates which were already recited above in connection with the composite of the present invention.

A contribution to solving the problems referred to at the beginning is also made by a composite obtainable by the process described above, this composite preferably having the same properties as the above-described composite according to the present invention.

A further contribution to solving the problems referred to at the beginning is made by chemical products comprising the water-absorbing composition of the present invention, the water-absorbing composition obtainable by the process according to the present invention or a composite according to the present invention. Preferred chemical products are in particular foams, moldings, fibers, foils, films, cables, sealing materials, liquid-imbibing hygiene articles, especially diapers and sanitary napkins, carriers for plant and fungal growth regulators or crop protection agents, additives for building products, packaging materials or soil additives.

Similarly, the use of the water-absorbing composition according to the present invention, of the water-absorbing composition obtainable by the process according to the present invention or of the composite according to the present invention in chemical products, preferably in the aforementioned chemical products, especially in hygiene articles such as diapers or sanitary napkins, and also the use of the superabsorbent particles as carriers for plant or fungal growth regulators or crop protection agents make a contribution to solving the problems referred to at the beginning. In relation to the use as carriers for plant or fungal growth regulators or crop protection agents, it is preferable for the plant or fungal growth regulators or crop protection agents to be released over a period controlled by the carrier.

The invention will now be more particularly elucidated with reference to test methods and non-limiting examples.

Test Methods

Determining the ΔL Value

The "L*" value is a measure of greyness (L=0 corresponds to black, L=100 corresponds to white). This scaling is based on the principles which are summarized in ASTM E 308 "*Standard Practice for Computing the Colors of Objects Using the CIE-System*".

The L variable is determined using a "Hunter LabScan XE" (Hunter Associates Laboratory, Reston, Va., USA) spectrophotometer at the following settings:

| | |
|---|---|
| "Mode" | 0/45 |
| "Area View" | 44.5 mm |
| "Port Size" | 50.8 mm |
| "UV-Filter" | nominal |

The LabScan XE is calibrated before every measurement by first clamping the black glass plate belonging to the instrument's accessories between the sample tray and the measurement opening, the glass plate being placed on a Petri dish (internal diameter 87 mm, depth: 14 mm) and the calibration with the black glass plate being effected by operating the "OK" switch. The white standard plate is then placed on the Petri dish in the same manner and the calibration is effected again by operating the "OK" switch.

After the calibration has been performed, the "Read Std" switch is pressed to test the functionability of the measuring instrument while the standard plate is still in place. The "Read" switch is then operated to measure the L variable for the standard plate.

The standard plate is subsequently removed and the Petri dish is filled with the water-absorbing polymeric structure to be measured, a blade being used to smooth the product surface. The sample is measured by pressing the "Read Sam" switch (=$L_0$ value). The sample is then stored in a conditioning cabinet at 70° C. and a relative humidity of 75% for 10 days. After this storage period, the L value is redetermined (=$L_1$ value). After 10 to days of storage in the conditioning cabinet, the sample was removed and measured without dish to determine the Hunter Color values of the resultant SAP pad (Lab). Because of the inhomogeneous color degradation of the sample following treatment in the conditioning cabinet, the measurement was carried out at 8 different locations. At the same time, the sample was photographed for comparison.

The following equation applies:

$$\Delta L = |L_1 - L_0|$$

Furthermore ΔL'-value will be determined, which is the difference of the $\Delta L_i$-value of comparison example 1 (Powder A with an oxidizing agent without the inhibitor) and ΔL-values of examples 1 to 3.

The following equation applies:

$$\Delta L' = |\Delta L - \Delta L_i|$$

EXAMPLES

Preparation Example 1

A monomer solution consisting of 320 g of acrylic acid, 248.649 g of NaOH (50% strength), 407.022 g of deionized water, 0.631 g of polyethylene glycol 300 diacrylate (having an active-substance content of 76.1 wt %) and 1.31 g of polyethylene glycol 500 O-monoallyl ether acrylate (having an active-substance content of 73.1 wt %) was freed of dissolved oxygen by purging with nitrogen and cooled down to the start temperature of 4° C. On attainment of the start temperature the initiator solution (0.3 g of sodium peroxodisulphate in 10.0 g of $H_2O$, 0.07 g of 35% strength hydrogen peroxide solution in 10.0 g of $H_2O$ and 0.015 g of ascorbic acid in 2.0 g of $H_2O$) was added. After the end temperature of about 110° C. had been reached, the resultant gel was comminuted with a meat grinder and dried in a drying cabinet at 150° C. for 2 hours. The dried polymer was coarsely crushed, ground by means of an SM 100 cutting mill equipped with 2 mm sieve and sieved to a powder having a particle size of 150 to 710 μm (=powder A).

The powder A was mixed with an aqueous solution consisting of ethylene carbonate (1 wt % based on powder A), aluminum lactate (0.3 wt % based on powder A), aluminum sulphate (0.3 wt % based on powder A) and water (3 wt % based on powder A) in a laboratory mixer and subsequently heated in an oven at 170° C. for 90 min.

Comparative Example 1 (Oxidizing Agent Only, No Inhibitor)

50 g of the water-absorbing polymer from Preparation Example 1 were mixed with 1.5 g of sodium percarbonate (Q35 Standard HPC from Evonik Industries) for 1 hour on a roll stand until homogeneous.

Example 1 (In Accordance with the Present Invention)

50 g of water-absorbing polymer from Preparation Example 1 were mixed with 1.5 g of sodium percarbonate (Q35 Standard HPC from Evonik Industries) and 0.125 g of HQME for 1 hour on a roll stand until homogeneous.

The above compositions were measured to determine their ΔL values. The results are summarized in the table below:

| Composition | ΔL value | ΔL' |
|---|---|---|
| Preparation Example | 13.0 | |
| Comparative Example 1 | 34.0 | |
| Example 1 | 1.0 | 33 |

The results show that HQME is able to distinctly reduce the severe color degradation due to sodium percarbonate (see Comparative Example 1).

Example 2 (In Accordance with the Present Invention)

50 g of water-absorbing polymer from Preparation Example 1 were mixed with 1.5 g of sodium percarbonate (Q35 Standard HPC from Evonik Industries) and 0.22 g of hydroquinone for 1 hour on a roll stand until homogeneous.

Example 3 (In Accordance with the Present Invention)

50 g of water-absorbing polymer from Preparation Example 1 were mixed with 1.5 g of sodium percarbonate (Q35 Standard HPC from Evonik Industries) and 0.41 g of 4,4'-oxydiphenol for 1 hour on a roll stand until homogeneous.

The above compositions were measured to determine their ΔL values. The results are summarized in the table below:

| Composition | ΔL value | ΔL' |
|---|---|---|
| Comparative Example 1 | 34.0 | |
| Example 2 | 10.0 | 24 |
| Example 3 | 5.0 | 29 |

The results show that hydroquinone, 1,4-dimethoxybenzene and 4,4'-oxydiphenol are able to distinctly reduce the severe color degradation due to sodium percarbonate (see Comparative Example 1) as well as HQME.

Comparative Example 2 (Oxidizing Agent Only, No Inhibitor)

50 g of the water-absorbing polymer from Preparation Example 1 were mixed with 4.88 g of sodium perchlorate for 1 hour on a roll stand until homogeneous.

Example 4 (In Accordance with the Present Invention)

50 g of water-absorbing polymer from Preparation Example 1 were mixed with 4.88 g of sodium perchlorate and 0.125 g of HQME for 1 hour on a roll stand until homogeneous.

The above compositions were measured to determine their ΔL values. The results are summarized in the table below:

| Composition | ΔL value |
|---|---|
| Comparative example 2 | ~22 |
| Example 4 | ~10 |

The results show that HQME is also able to distinctly reduce the severe color degradation due to sodium perchlorate (see Comparative Example 2).

Experimental Description of "Post-Treatment with Sodium Percarbonate & HQMe"

Comparative Example 3 (No Oxidizing Agent, No Inhibitor)

50 g of the water-absorbing polymer from Preparation Example 1 and 50 g of the pre-product (Powder A) before the surface crosslinking were used.

Comparative Example 4 (Oxidizing Agent Only, No Inhibitor)

A 1, 5 g quantity of sodium percarbonate (Q35 Standard HPC) was weighed (after crushing with mortar & pestle, since very coarse) into a 125 mL twist lid glass (using a weighing boat). A 50 g quantity of the pre-product (powder A) respectively the postcrosslinked SAP material was added to inhibitor and the sample was homogenized on a roll stand for at least 1 h.

Comparative Example 5 (Inhibitor Only)

A 0.125 g quantity of HQME for synthesis was weighed (after crushing with mortar & pestle, since very coarse) into a 125 mL twist lid glass (using a weighing boat). A 50 g quantity of postcrosslinked SAP material was added to inhibitor and the sample was homogenized on a roll stand for at least 1 h.

Example 5

A 0.125 g quantity of HQME for synthesis was weighed (after crushing with mortar & pestle, since very coarse) into a 125 mL twist lid glass (using a weighing boat). Then, 1.5 g of sodium percarbonate (Q35 Standard HPC) were added thereto without further pretreatment. A 50 g quantity of postcrosslinked SAP material according to preparation example 1 was added to this mixture and the sample was homogenized on a roll stand for at least 1 h. In another example the pre-product (powder A) of the preparation example 1 was added to this mixture.

The samples thus obtained were transferred in an analytical laboratory into a Petri dish from Greiner so that the dish was initially overfull. The superabsorbent was skimmed off with a ruler in order that the dish may be full to the rim. The Lab value of the absorbent was then measured through the dish at 4 different locations and averaged. The sample was then photographed, the dish was loosely covered with the lid and placed in a conditioning cabinet at 70° C. and 75% relative humidity. After 20 days of storage in the conditioning cabinet, the sample was removed and measured without dish to determine the Hunter Color values of the resultant SAP pad (Lab). Because of the inhomogeneous color degradation of the sample following treatment in the conditioning cabinet, the measurement was carried out at 8 different locations. At the same time, the sample was photographed for comparison.

TABLE

ΔL values of variously treated samples following storage in conditioning cabinet for 20 days

| | ΔL values | ΔL values |
|---|---|---|
| | Sample | |
| | Precursor product 20 days | SX product 20 days |
| Preparation example (without post-treatment) | 36 | 9 |
| comparative example 3 (just 3% of percarbonate) | 52 | 39 |
| comparative example 4 (just 0.25% of HQME) | 15 | 16 |
| Example 5 (3% of PC plus 0.25% of HQME) | 4 | 12 |

The invention claimed is:

1. A water-absorbing composition comprising at least: i) from 91.2 to 98.9 wt % of at least one water-absorbing polymer; ii) from 1 to 8 wt % of at least one oxidizing agent; and iii) from 0.1 to 0.75 wt % of at least one inhibitor to inhibit free-radical polymerizations; wherein the inhibitor is a hydroquinone or a hydroquinone derivative selected from the group consisting of hydroquinone, hydroquinone monomethyl ether (HQME), 1,4-dimethoxybenzene, 4,4'-oxydiphenol and a mixture of two or more thereof; and wherein the weight quantities are each based on the overall weight of the water-absorbing composition.

2. The water-absorbing composition according to claim 1 wherein the water-absorbing polymer i) is particulate and at least 90 wt % of the particles of the water-absorbing polymer i) have a particle size in a range from 150 to 850 μm.

3. The water-absorbing composition according to claim 1 wherein the oxidizing agent ii) is a hydrogen peroxide source.

4. The water-absorbing composition according to claim 3 wherein the oxidizing agent ii) is a percarbonate.

5. The water-absorbing composition according to claim 1 wherein the composition in addition to the components i) to iii) further comprises a bleach activator iv).

6. The water-absorbing composition according to claim 5 wherein the bleach activator iv) is selected from the group consisting of tetraacetylethylenediamine (TAED), nonanoylbenzenesulphonate (NOBS) and a mixture of two or more thereof.

7. The water-absorbing composition according to claim 1 wherein the composition has a measure of greyness, ΔL, value of at most 10.0 after the water-absorbing composition has been stored at 70° C. and a relative humidity of 75% for 10 days.

8. A process for producing a water-absorbing composition, comprising at least the steps of: (I) providing 91.2 to 98.9 wt. % of at least one water-absorbing polymer; (II) contacting the at least one water-absorbing polymer with 1 to 8 wt. % of at least one oxidizing agent; and (III) contacting the at least one water-absorbing polymer with 0.1 to 0.75 wt. % of at least one inhibitor to inhibit free-radical polymerizations; wherein step III) can be carried out before, during or after step II); and wherein the inhibitor is a hydroquinone or a hydroquinone derivative selected from the group consisting of hydroquinone, hydroquinone monomethyl ether (HOME), 1,4-dimethoxybenzene, 4,4'-oxydiphenol and a mixture of two or more thereof; and wherein the weight quantities are each based on the overall weight of the water-absorbing composition.

9. The process according to claim 8 wherein the water-absorbing polymer is particulate and at least 90 wt % of the particles of the water-absorbing polymer have a particle size in a range from 150 to 850 μm.

10. The process according to claim 8 wherein the oxidizing agent is a hydrogen peroxide source.

11. The process according to claim 10 wherein the oxidizing agent is a percarbonate.

12. The process according to claim 8 wherein the process comprises the further step of: IV) contacting the at least one water-absorbing polymer with at least one bleach activator.

13. The process according to claim 12 wherein the bleach activator is selected from the group consisting of tetraacetylethylenediamine (TAED), nonanoylbenzenesulphonate (NOBS) and a mixture of two or more thereof.

14. The water-absorbing composition obtainable by a process according to claim 8.

15. The water-absorbing composition according to claim 14 wherein the composition has a measure of greyness, ΔL, value of at most 10 after the water-absorbing composition has been stored at 70° C. and a relative humidity of 75% for 10 days.

16. A process for producing a composite, said process comprising bringing a water-absorbing composition according to claim 1, a substrate and optionally an auxiliary into contact with each other.

* * * * *